United States Patent
Wefler

(10) Patent No.: US 6,853,801 B2
(45) Date of Patent: Feb. 8, 2005

(54) MODULAR ELECTRICAL DEVICE FOR DELIVERY OF VOLATILE COMPOUNDS

(75) Inventor: Mark E. Wefler, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 10/381,585

(22) PCT Filed: Sep. 26, 2001

(86) PCT No.: PCT/US01/30035

§ 371 (c)(1),
(2), (4) Date: Mar. 26, 2003

(87) PCT Pub. No.: WO02/26274

PCT Pub. Date: Apr. 4, 2002

(65) Prior Publication Data

US 2004/0005146 A1 Jan. 8, 2004

Related U.S. Application Data

(60) Provisional application No. 60/235,357, filed on Sep. 26, 2000.

(51) Int. Cl.[7] .................................................. F24F 6/00
(52) U.S. Cl. ....................................... 392/392; 392/390
(58) Field of Search ................................. 392/386, 390, 392/392, 394, 395; 439/11, 13, 638, 650, 651, 652, 654

(56) References Cited

U.S. PATENT DOCUMENTS

| | | | | |
|---|---|---|---|---|
| 2,611,068 A | | 9/1952 | Wellens | 219/19 |
| 2,636,096 A | * | 4/1953 | Di Blasi | 337/189 |
| 3,780,260 A | | 12/1973 | Elsner | 219/271 |
| 3,951,487 A | * | 4/1976 | Waldbrook | 439/21 |
| 4,804,821 A | * | 2/1989 | Glucksman | 392/390 |
| 4,979,907 A | | 12/1990 | Lee | 439/214 |
| 5,038,394 A | * | 8/1991 | Hasegawa et al. | 392/395 |
| 5,926,614 A | | 7/1999 | Steinel | 392/392 |

FOREIGN PATENT DOCUMENTS

EP    0 976 410 A1    12/1998

* cited by examiner

*Primary Examiner*—Sang Paik

(57) ABSTRACT

A means is provided for manufacture of dispensers of volatile materials for various regions, where a single buss assembly strip is provided, having standardized electrical connections whereby the manufacturer, distributor, or consumer is enabled to construct a large variety of finished dispensers by choice of individual selected attachment modules providing differing functions. For example, one may combine the buss assembly strip with a modular plug assembly for use in a specific region of the world, with optional heaters, night lights, timers, switches, and controls.

10 Claims, 7 Drawing Sheets

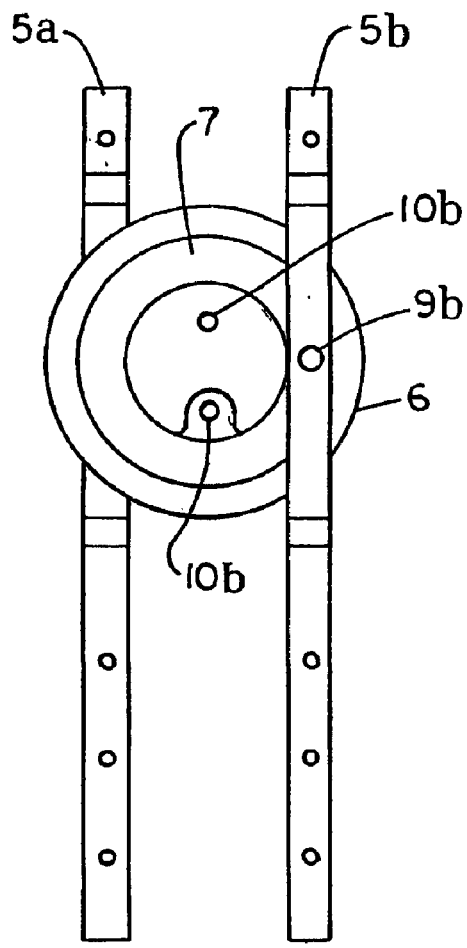
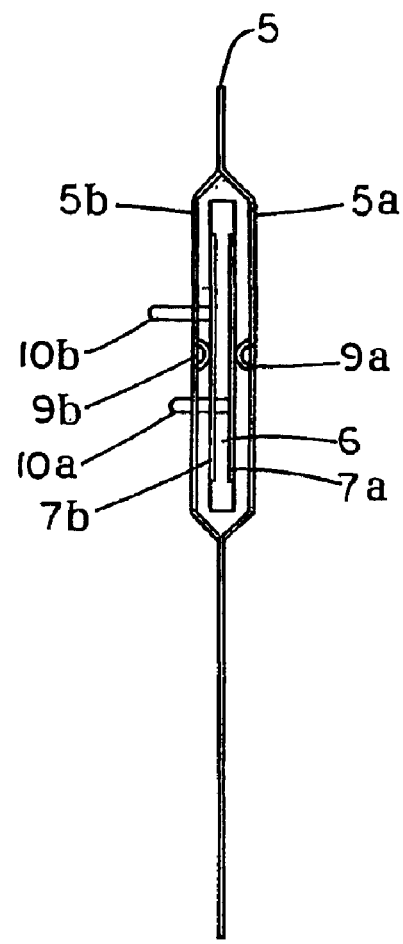
FIG. 3          FIG. 4
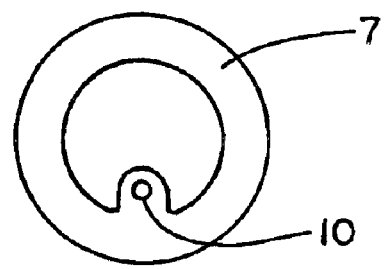
FIG. 5

MODULAR ELECTRICAL DEVICE FOR DELIVERY OF VOLATILE COMPOUNDS

CROSS-REFERENCE TO RELATED APPLICATIONS

This Application claims priority of U.S. Provisional Application No. 60/235,357, filed Sep. 26, 2000, previously entitled GLOBAL MODULAR LIQUID WICK SYSTEM.

FEDERALLY SPONSORED RESEARCH OR DEVELOPMENT

Not Applicable

BACKGROUND OF THE INVENTION

The present invention relates to a modular electrical device for the delivery of volatile compounds. Various electrically powered devices are used for the delivery of volatile compounds such as air-fresheners and insecticides. Typically these devices are powered by battery or line current, and have a source of heat to volatilize either a wicked liquid, a gel, or a solid containing a fragrance or insecticide. Recently these devices have incorporated certain additional features, such as fans to disperse the volatile compound; night light devices; on-off switches; controls for increasing or decreasing the heat generated by the device and accordingly the amount of volatile material given off; controls for opening or closing apertures and thus controlling air flow and the amount of chemical volatilized; end use indicators; and the like. Because these devices are used in different countries where electrical requirements are different, the devices are also manufactured with different plugs, differing resistance units to generate heat, and/or different voltage light elements, such as for instance those for use in North America, and those for usage in, for example, Europe or Asia.

The complexity and variety of the various items that can be added to the devices has created a problem for both consumers and manufacturers in the assembly, storage of component parts, and the like, because of the diversity of possibilities. The standardization of components, and of a common electrical supply source to which the components might be attached would increase the efficiency of manufacture, lower the cost of manufacture of these devices, and allow for greater variety of choice among additional components by the consumer. This invention is directed to a modular system for the manufacture and construction of electrically powered dispensers to be used to volatilize components such as fragrances and insecticides. While the invention is described in terms related to this specific usage, other usages of the invention set forth are clearly possible. The devices are preferably line voltage powered, but may be powered by batteries, but most have one common element: a source of heat, generally from a resistance element, that helps to volatilize the fragrance or insecticide.

Of interest with respect to the present invention are wicking dispenser devices in which the wicking action is promoted by a heat source. This type of wicking device is described in, among others, U.S. Pat. Nos. 1,994,932; 2,597,195; 3,288,556; 3,431,393; 3,482,929; 3,633,881; 4,020,321; 4,968,487; 5,290,546; and 5,364,027; all of which are incorporated herein by reference.

Additional dispensers of the type often referred to as plug-in diffusers are described in U.S. Pat. Nos. 4,849,606, and 5,937,140, which are assigned to S.C. Johnson & Son, Inc., of Racine, Wis., both of which are incorporated herein by reference. Of these references, it is noted that U.S. Pat. No. 5,937,140 discloses a fragrance warmer incorporating plug-though capability. The present invention constitutes an improvement upon this reference, optionally permitting addition of an integral night light feature and novel electrical circuitry, and other features, in a unit providing for simpler, less expensive assembly.

In addition to the above, Luthy discloses, in U.S. Pat. No. 4,837,421, a fragrance dispenser which releases a fragrance from a solid polyamide resin body. The dispenser includes a housing, having at least one opening, disposed adjacent to the resin. A heating resistor is provided in the housing for maintaining an elevated temperature, and a thermally conductive metal heating plate is arranged in the housing in thermally conductive relationship with the heating resistor and configured to at least partially surround and contact the resin body containing the fragrance.

Wang, in U.S. Pat. No. 5,556,192, discloses a perfumer with an optically controlled night lamp. The perfumer includes a heat conductor wrapped by a heat conductive and fireproof plastic material for generating heat to vaporize a solid perfume, and uniformly disperse the perfume gas. The night lamp is disposed within the perfumer structure and is controlled by an optically sensitive element which turns the lamp on or off in accordance with ambient illumination. The perfumer is powered by a power plug consisting of a pair of identical copper plates having a heat conductor welded there between to form a circuit.

In addition, the incorporation of night lights into electrical vaporizers is also taught in U.S. Pat. Nos. 2,942,090, of Diehl, U.S. Pat. No. 3,780,260, of Elsner, and U.S. Pat. No. 4,084,079, of Costello. These references, however, fail to provide the conveniences and economies of the present invention.

As indicated, it is well known to provide electrical heating devices for dispensing such materials as air fresheners, deodorizers, and insect control materials. Such devices may often comprise a liquid reservoir of liquid to be dispensed, an electric heater to warm the liquid to cause it to vaporize more readily, and an electrical plug to plug the device into an electric outlet for power.

One example of such a dispenser is taught by U.S. Pat. No. 5,038,394, of Hasegawa et al. This reference teaches a cordless thermal vaporizer of the liquid type wherein the body of the vaporizer has a heater for heating a wick for drawing up a chemical solution from a bottle, and a socket disposed under the heater and removably fittable in the form of a cap to the bottle for attachment thereto. The body is reduced in weight and thereby made attachable to an electric outlet with stability. The solution bottle can be attached directly to the socket of the body and is easy to replace. Thus, the patent relates to a thermal vaporizer in which an electric wick warmer is near the top of the assembly, with a bottle containing the vaporizable chemicals suspended below. The reference, in addition, teaches that the plug, located on the back of the vaporizer body, may be rotated through a range of from 0 to 90 degrees to make the arrangement of the plug blades selectively changeable to either a vertical or horizontal orientation, so as to make the vaporizer suitable for use in either vertically or horizontally oriented electrical outlets, a highly desirable option In addition, U.S. Pat. No. 5,647,053 of Schroeder et al teaches a vapor dispensing device comprising an electric wick warming block in conjunction with a container of liquid to be dispensed, in which the electric plug is rotatable about an axis parallel to the plug pins. This type of dispenser is exemplary of features provided more conveniently and economically through use of the present invention. The disclosure of this patent and all other publications referred to herein are incorporated herein by reference as if fully set forth herein.

BRIEF SUMMARY OF THE INVENTION

The invention provides a modular system for the manufacture and construction of electrical devices used for the dispensing of volatile components into the atmosphere. These volatile components are generally air fresheners or deodorizers and/or insecticides. Electrical devices used for the dispensing of air fresheners or deodorizers and/or insecticides are well known and are commercially available from a variety of sources. As stated above, while most of these devices have a common element, generally a heat source, preferably a resistance heater, other components on the device vary with the type of volatile compound to be dispersed into the atmosphere, the sophistication required for the use selected, the control of the heat source, and for esthetic or other utilitarian features such as fans, night lights and the like.

These devices have typically been made by assembling such components into a finished dispenser device and providing the assembled device in a package or container which may be decorative or utilitarian in nature, for sale to the consumer. The present invention is therefore directed to a system for combining such individual components in a manner in which the local supplier or manufacturer may customize the product to meet regional consumer needs and electrical requirements, and in which the distributor or even the consumer may pick and choose those components to be present in the device assembled for use. Thus, the present invention comprises a global buss assembly chassis, to which a variety of individual modules may be added or attached, and the various individual modules for use with the global buss assembly chassis. The individual modules may comprise such elements, either individually or in combination, as heaters, fans, night lights, on/off switches, programmable controls, extra electrical outlets, and plugs designed specifically to meet regional requirements. The present invention is not meant to be limited by the type of container used to cover or conceal the working parts of the device, or by the specific nature of the volatile component to be dispersed to the atmosphere. Because of the variety of components necessary for a world-wide market, where electrical voltages vary, where electrical plugs are different in different regions, and where even a night light bulb may have to be changed because of a voltage difference, the assembly of these devices for a world-wide consumer market has been costly. This invention is intended to simplify the manufacture, design and construction of such devices.

BRIEF DESCRIPTION OF THE DRAWINGS

FIG. 3 is a simplified drawing showing the relationship between the buss bars and the rotatable plug elements of the buss assembly of FIG. 2.

FIG. 4 is a cross-sectional view on line IV—IV of FIG. 2.

FIG. 5 is a front view of the contact ring of the rotatable plug unit.

DETAILED DESCRIPTION OF THE INVENTION

Figure 1:
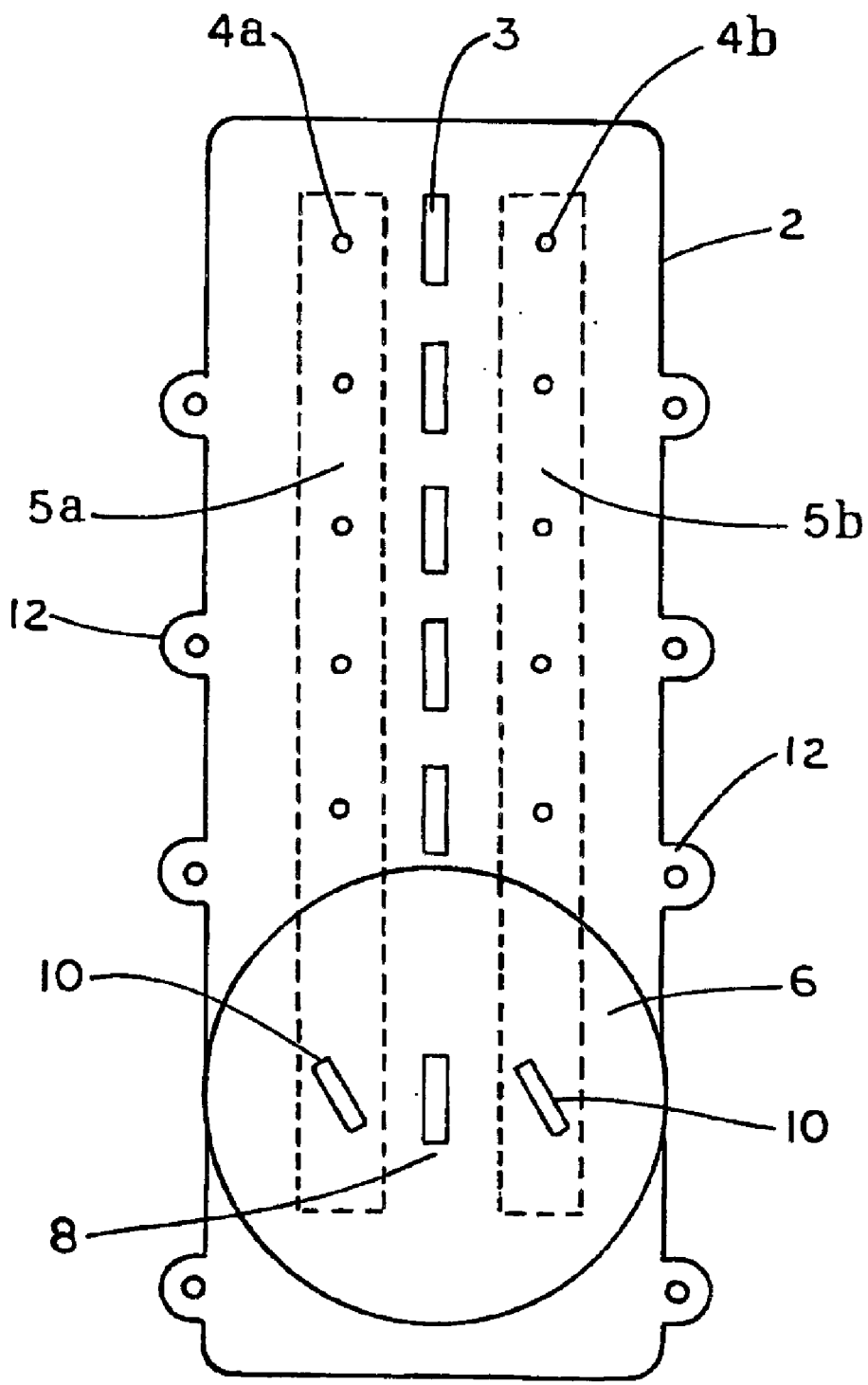
FIG. 1 is a rear view of an electrical buss assembly strip having standardized openings designed for the attachment of modular components.

Referring to the drawings, FIG. 1 is a simplified diagram of a modular buss assembly strip, 2, for a device in accordance with this invention. Buss assembly 2 is constructed of an electrically insulating material such as a non-conductive plastic. Buss assembly 2 is constructed with openings 3 to be engaged by modular devices, not shown in FIG. 1, which may engage attachment openings 3, and electrical contact points 4 which may be engaged with said modular devices to conduct power to such devices. Buss assembly strip 2 may have any number of openings 3, each accompanied by two or more electrical contact points 4 to allow attachment and electrical connection of modular devices on either the front or rear side thereof. For purposes of the present description, the term "front" of the buss assembly shall be taken to mean the face of the buss assembly, 2, which faces outward into the room when the buss assembly is attached to an electrical outlet, as in a wall outlet. Conversely, the terms "back" or "rear" of the buss assembly shall be taken to refer to that side of the buss assembly which faces the outlet or wall. As will be appreciated by one skilled in the art, attachment hole 3 may be rectangular, as shown, or may be of any shape designed to accept a fastener such as a plastic pin, a screw, or the like. It is not important what type of fastener is utilized so long as modular devices may be fastened so that their respective electrical contacts appropriately engage electrical contact points 4.

The buss assembly, 2, may be seen to comprise buss bars 5a and 5b. Contact points 4a and 4b, in said buss bars 5a and 5b, constitute positive and negative electrical contacts for connection of modular devices, not shown in FIG. 1, which are designed with fastening mechanisms for attachment to, or engagement with, attachment hole 3, and appropriate means to engage electrical contact points 4a and 4b for conduction of electrical power. While the contact points, 4, are illustrated in the figures as being cylindrical receptacles or holes for insertion of corresponding conductive pins, it is to be understood that they could also be of other shapes, such as a rectangular receptacle for the blade shape of a typical electrical plug. Moreover, rather than being receptacles into which pins or blades may be inserted, such electrical contact points may themselves constitute pins or blades perpendicular to and extending outward from the front of the buss bars to engage receptacles in the modular device to be attached. That is, electrical contact points 4 may constitute either male of female electrical plug elements, for engagement of modular devices of the appropriate opposite interactive configuration. More than two contact points may be provided to allow attached modular devices to be grounded.

Modular buss assembly 2 is also provided with rotatable plug assembly 6. Rotatable plug assembly 6 may optionally be designed with an attachment hole 8, similar to the attachment holes 3, and has electrical contact elements 10, similar to electrical contact points 4, which permits a standard electrical plug, not shown, to be fastened to rotatable plug 6, by which the modular buss bar may be connected to a typical wall outlet. A standard electrical plug module may engage electrical contact elements 10, and thus provide power to electrically conductive buss bar elements 5a and 5b, in the form of conductive strips, or wires, within the buss assembly strip 2, which provide power to electrical contact points 4a and 4b, respectively. As indicated previously, electrical contact points 4 can be designed as male or female elements, or a combination of contact points 4 can be designed with both male and female elements to allow proper installation of modular devices. As shown in FIG. 1, the buss assembly 2 may be equipped with contact points 4 on its front and/or rear sides to allow for placement of devices on either side of the bar. Likewise, attachment hole 3 may preferably pass entirely through the assembly, to allow for placement of devices on either front or rear. While the buss assembly unit as shown is equipped with a rotatable plug, 6, it will be appreciated by those skilled in the art that the rotatable plug may also be replaced with one or more batteries to provide power to the bus. Also shown in FIG. 1 are mounting points, 12, for assembly of modular units, such as, for example, attachment of cover elements. Still further, it is with the scope of the present invention to provide a buss assembly strip having a fixed or predetermined plug element, by which the buss assembly strip may be plugged into the electrical circuitry of the region for which it is intended.

Figure 2:
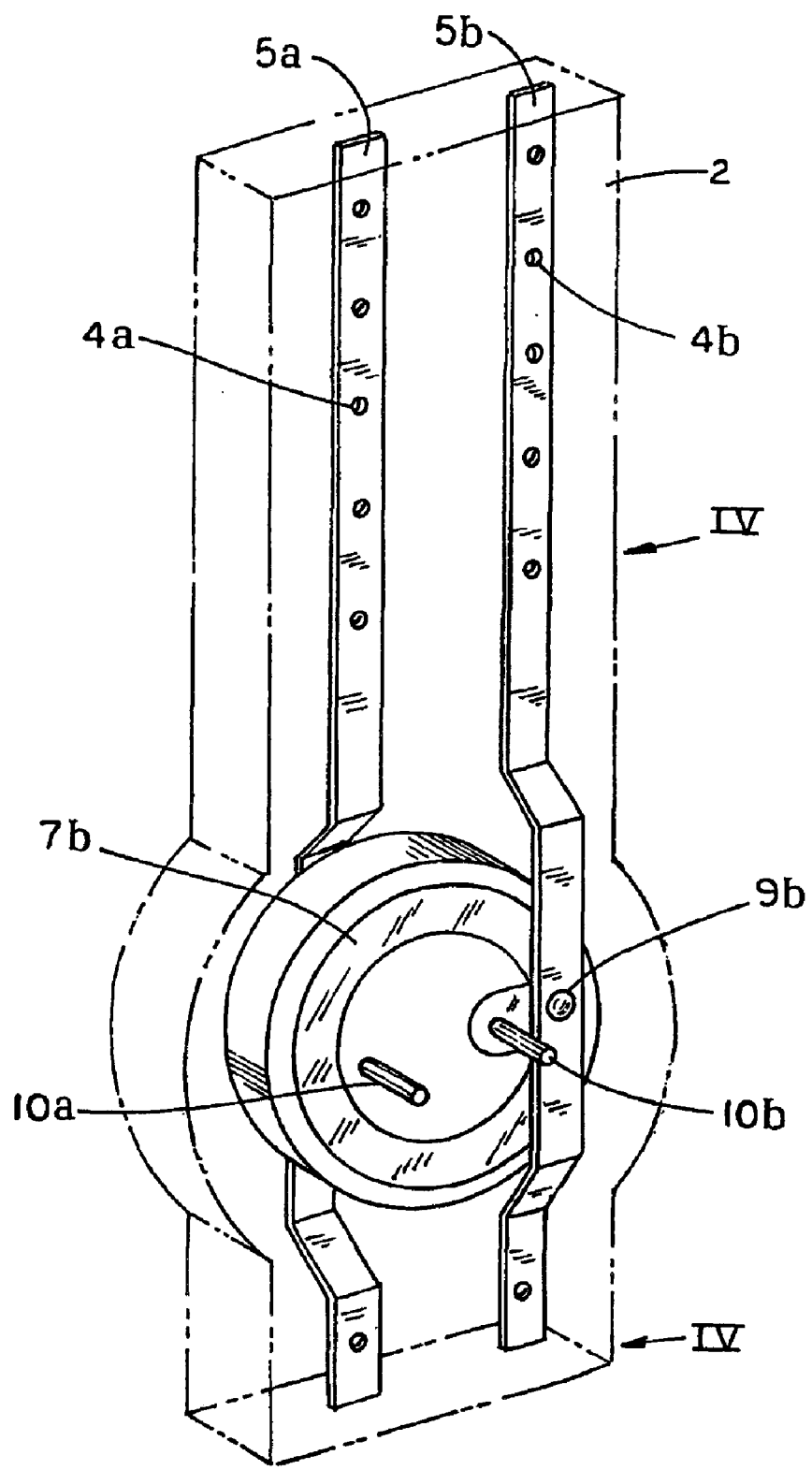
FIG. 2 is a rear perspective view of the internal components of a preferred embodiment of the buss assembly strip.
Figure 9:
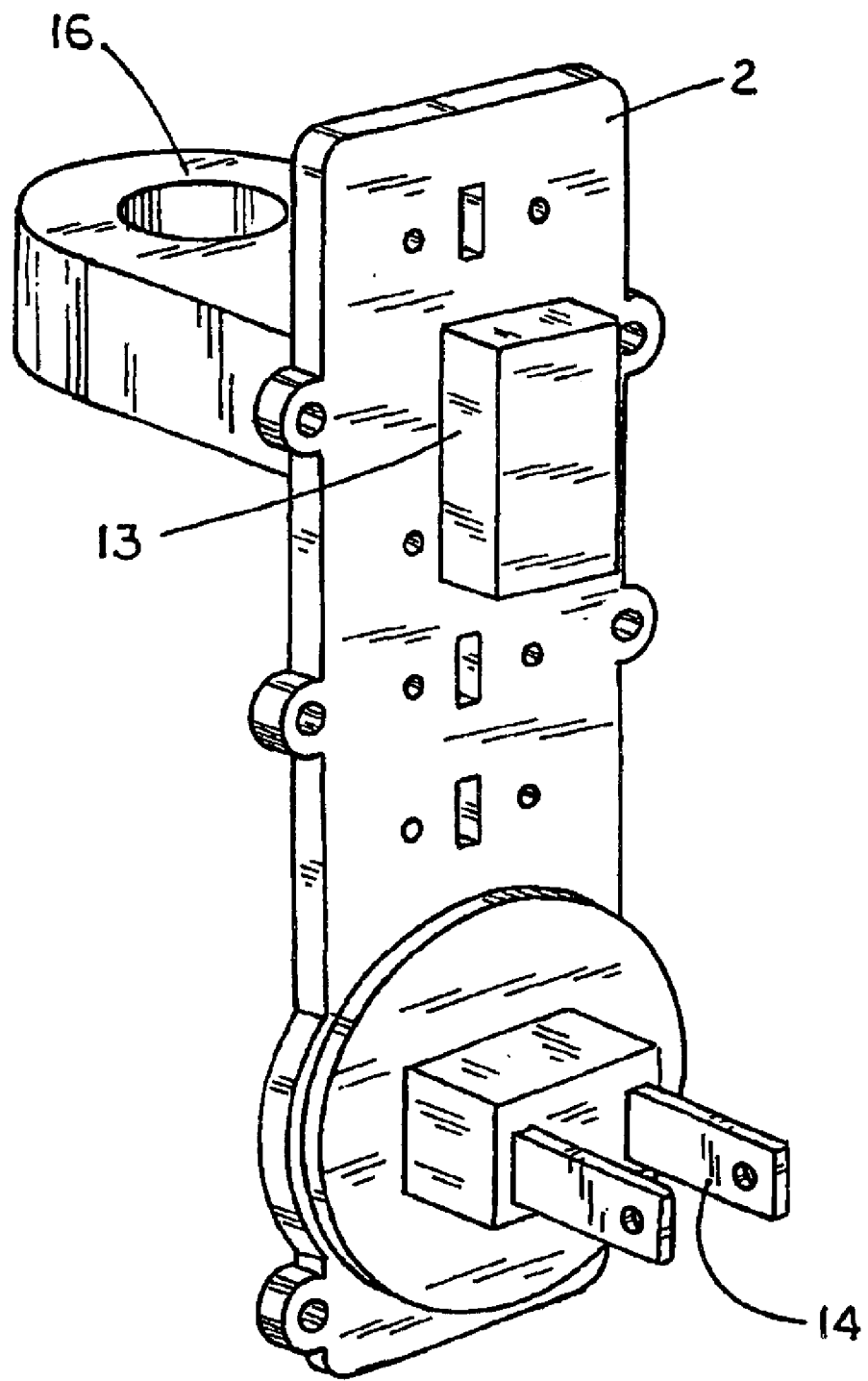
FIG. 9 is a simplified rear view of the modular buss assembly strip having a programmable module and a conventional plug module attached thereto.

As shown in FIGS. 2 through 4, buss bars 5a and 5b comprise similar strips of conductive material, preferably metallic, and most preferably copper, which encompass contact points 4a and 4b, and contact the rotatable plug 6, and provide, as appropriate, live and neutral electrical connectors. The rotatable plug element preferably is provided with male contact points, 10a and 10b, which engage a modular electrical plug element 14, such as shown in FIG. 9. While contact points 10a and 10b could optionally be female electrical contact elements, it is preferred that they be male electrical contact elements. A modular plug element, 14, is so designed as to be plugged into the electrical outlet commonly in use in the region for which the modular unit is intended, and thus may have a variety of configurations. When such a modular plug element, attached to a rotatable plug of the modular buss assembly described herein, is inserted into an outlet, electrical power is thus provided, via contact points 10a and 10b, to the rotatable plug assembly and to the conductive buss bar elements 5a and 5b, and thus to the electrical contact points, 4a and 4b, in each of said conductive elements 5a and 5b. When an electrical heater, fan, switch, or other optional modular electrical implement is then connected to the contact points, 4, by attaching the modular element thereto, a complete electrical circuit may be created, and said heater, fan, switch, etc., will be activated electrically. The electrically conductive strip buss bar 5, of buss assembly strip 2, can be prepared from a stamped metal, preferably aluminum, copper or brass and then covered with an insulating material. The electrically conductive element or path of buss bar 5 can also be nothing more than a flexible wire routed through supports, not shown. When a wire electrically conductive path is utilized, electrical contact points 4 may preferably be in the shape of a tuning fork so as to electrically engage the wire.

Contact elements 10 are thus designed to provide power to electrically conductive elements within the bus, thus providing a source of electricity to contact points 4. The offset nature of the bus bars of the buss assembly strip, and the means of providing contact with the rotatable plug, as shown in FIG. 2, is considered to provide a full 360 degree range of rotation with no interruption of power, and to maintain polarity throughout 360 degrees of rotation, and to provide a simpler, less expensive manner in which a circuit may be provided.

In FIG. 2, the offset nature of the buss bars is clearly indicated. As illustrated, the buss bar indicated as 5a passes on one side of the rotatable plug assembly, 6, while the buss bar identified as 5b passes on the other side of the rotatable plug. The rotatable plug itself constitutes a nonconductive material, having conductive contact rings 7a and 7b on the respective sides thereof. The conductive contact ring, 7, is shown in FIG. 5, wherein the electrical contact element 10 may be seen as being in direct electrically conductive contact with the ring itself. Identical conductive contact rings may be utilized on opposite sides of the rotatable plug. When a modular plug unit is attached to and establishes electrical connection with electrical contact members 10a and 10b of the rotatable plug assembly, electrical current will flow from contacts 10a and 10b to conductive rings 7a and 7b, respectively, on opposite sides of the rotatable plug. Each of rings 7a and 7b is in turn in contact with a buss bar, 5a and 5b respectively, through contact of the buss bars with the conductive rings on the opposed faces of the rotatable plug. Electrical contact between the conductive rings, 7a and 7b, and the buss bars, 5a and 5b, respectively, may be made by such means as a dimpled area in the buss bar, as shown at 9a and 9b, or by other means such as simple contact, brush connection, etc. The current may then be distributed through out the buss bars to electrical contacts 4, from which it may be conducted to modular units affixed thereto, as shown in FIG. 9.

In FIG. 3, a simplified representation of the invention illustrates again the offset nature of the buss bars, 5a and 5b. In this figure, buss bar 5a passes behind the rotatable plug 6, making electrical contact with the conductive contact ring on that side of the plug. Buss bar 5b passes in front of the rotatable plug 6, making contact with the conductive contact ring 7 on the side of the plug shown, via electrical contact dimple 9b. It is to be noted that the rotatable plug as shown in FIG. 3, has been turned 90 degrees, so that the electric contact elements 10a and 10b may be seen more clearly. The contact point 10b is shown as being in direct electrical contact with conductive contact ring 7 on the side of the rotatable plug shown, while the contact point 10a extends outward from the rear of the rotatable plug, as shown, for connection to a modular plug unit by which electrical power may be provided to the buss assembly. Contact point 10a contacts the conductive contact ring on the opposite side of the rotatable plug, whereby electrical current may be passed to the corresponding buss bar, 5a.

FIG. 4 represents a side elevation taken on line IV—IV of FIG. 2. This drawing clearly illustrates the offset nature of the buss bars, 5a and 5b, as well as the contact elements 9a and 9b, by which electrical current passes from an external plug module, not shown, which attaches to contact elements 10a and 10b, via conductive contact rings 7a and 7b.

Figure 6:
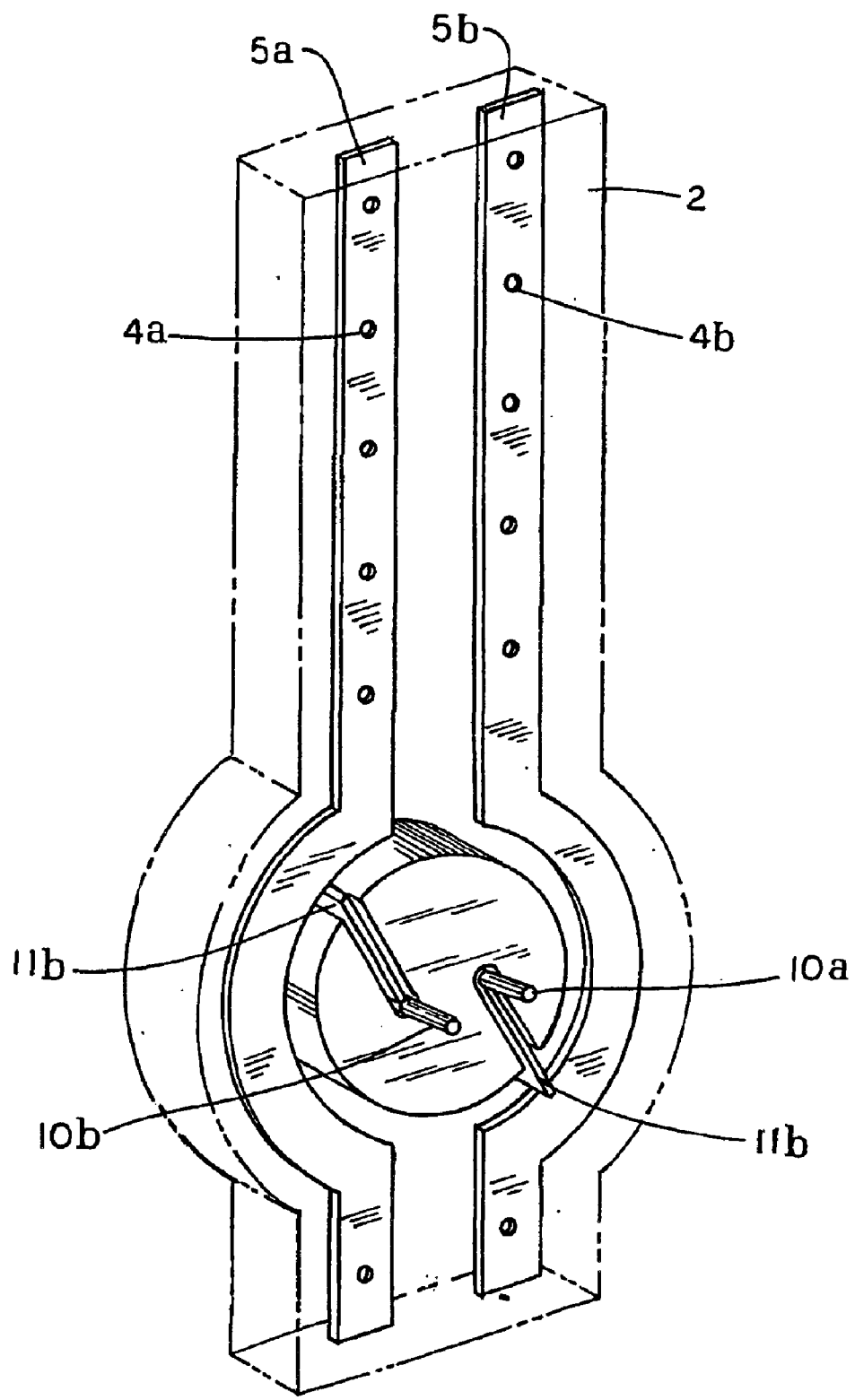
FIG. 6 is a rear perspective view of the internal components of a second embodiment of the buss assembly strip.

In FIG. 6, an alternative embodiment of the invention is illustrated. This figure represents a rear perspective view of the components of an alternative buss assembly strip, wherein the buss bar elements, 5a and 5b, are curved so as to pass around opposite sides of the circumference of the rotatable plug. As will be appreciated by one skilled in the art, during rotation of the rotatable plug, a null point or point of no electrical contact, will occur when the contact blades, 11a and 11b, reach the area between buss bars 5a and 5b, and no longer conduct power so said buss bars, as more clearly shown in FIG. 7. The existence of this gap between the buss bars, and the accompanying loss of electrical contact, results in the buss assembly strip being unpowered for certain positions of the rotatable plug. This embodiment may also be appropriate when electrical polarity is not required, since it would reverse polarity upon rotation of 180 degrees. Such buss assembly strips may be useful for most utilities and consumers, and do represent a more economical embodiment. As in the case of the preferred embodiment previously discussed, a modular electrical plug element may be connected to, and electrically continuous with, electrical contact elements 10a and 10b of the rotatable plug assembly illustrated in FIGS. 6 and 7. When electrical current flows from an external electrical outlet into which such a modular electrical plug element is inserted, current will flow via contact elements 10a and 10b through contact blades, 11a and 11b, to buss bars 5a and 5b. From the buss bars, electricity may then be provided to the optional modules of the consumers choice, such as a fan, a heater element, a night light, a power switch, etc, via electrical contact points 4a and 4b to which such modules are connected.

Figures 7, 8:
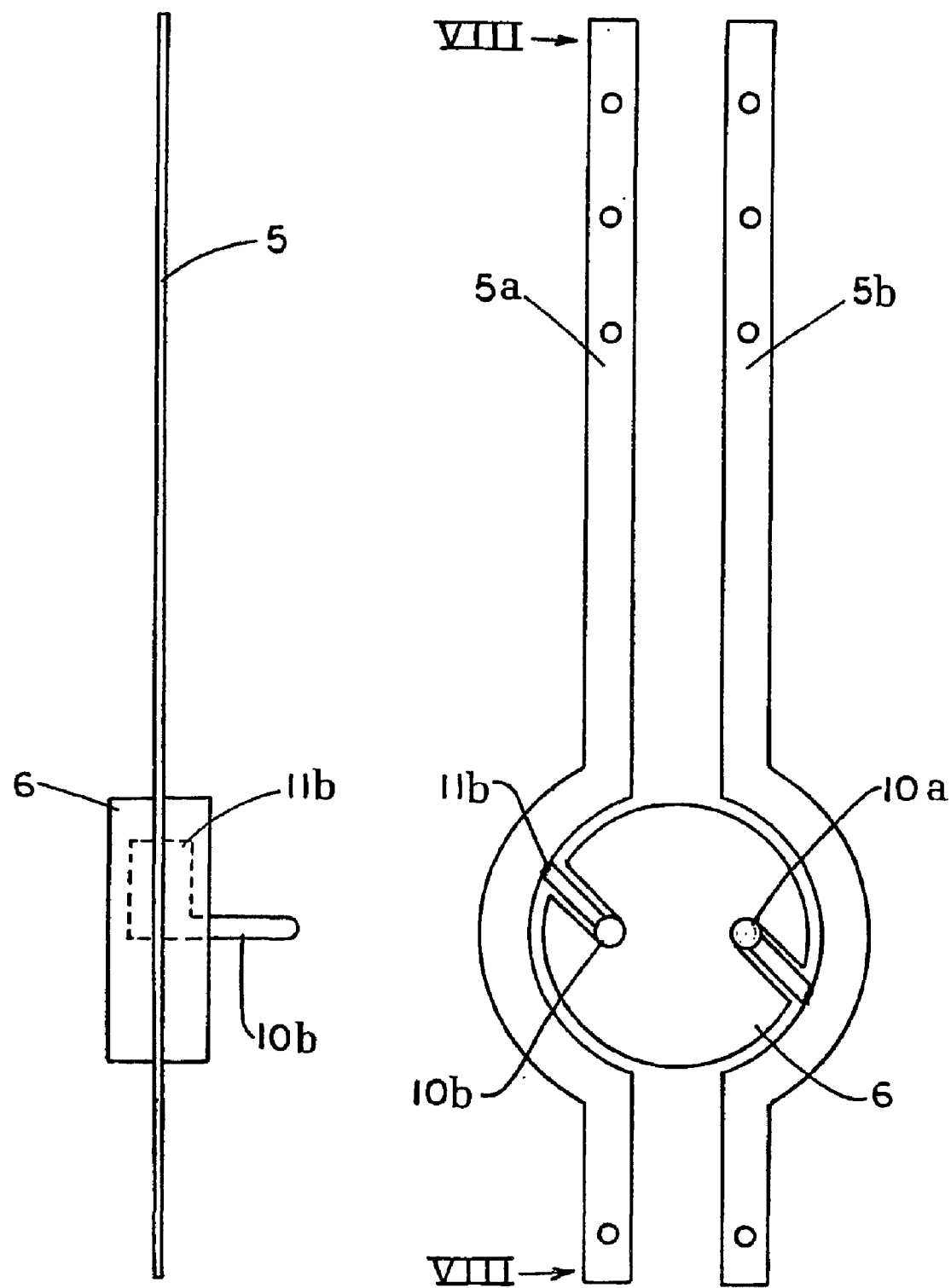
FIG. 7 is a simplified drawing showing the relationship between the buss bars and the rotatable plug elements of the buss assembly of FIG. 6.
FIG. 8 is a cross-sectional view on line VIII—VIII of FIG. 7.

FIG. 8, a sectional view from line VIII—VIII in FIG. 7, demonstrates the contact of blade 11b with the portion of buss bar 5a with which it is associated. The electrical power provided to contact element 10b is thus transmitted to the buss bars, and hence to an optional module attached to electrical contact points 4.

In FIG. 9, there is shown in conjunction with the modular buss assembly strip, 2, a programmable module 13, specifically designed to provide cyclic operation of the modular heater device 16 attached to the other side of the assembly strip. Also illustrated is the modular plug element 14, attached to the electrical contact elements 10a and 10b of rotatable plug 6, said contact elements not shown.

Figure 10:
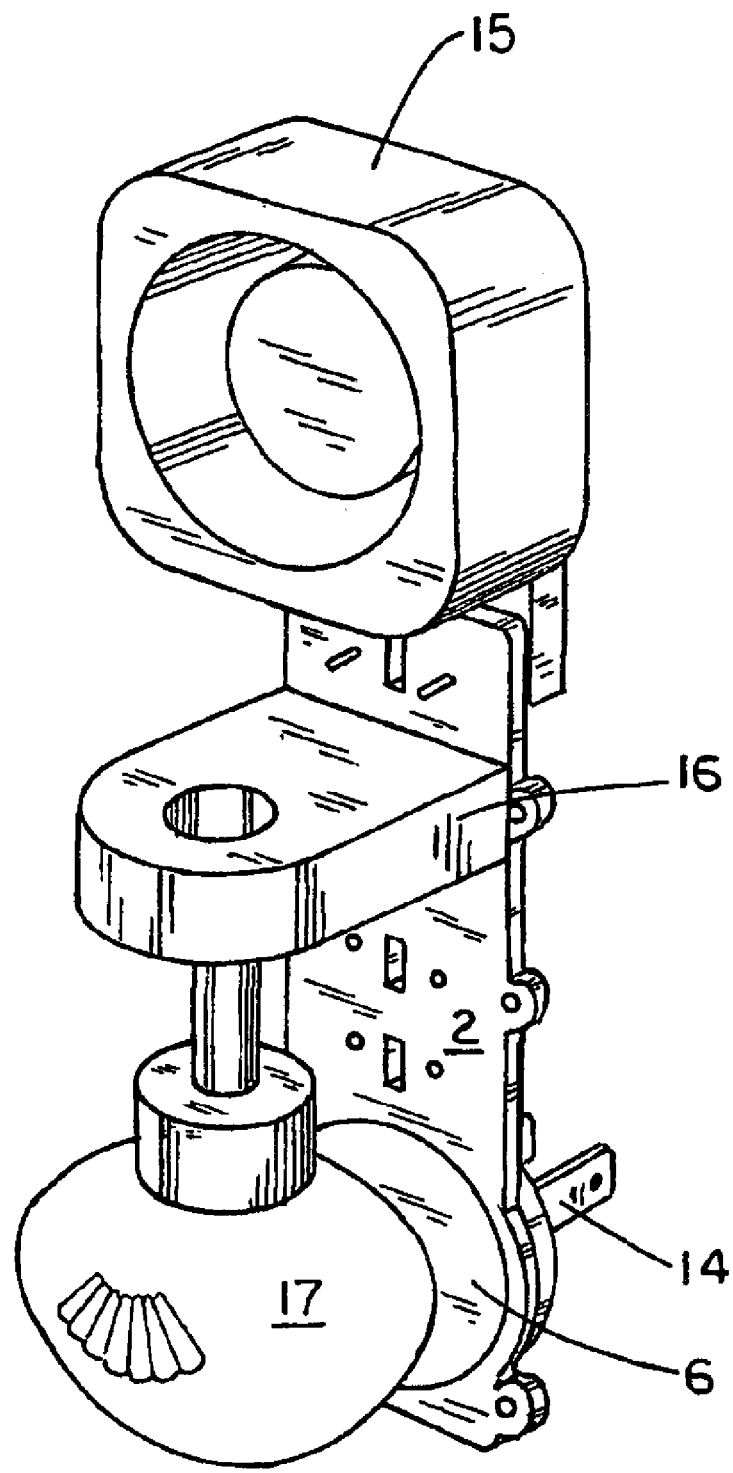
FIG. 10 is a simplified front perspective view illustrating the use of a fan module in combination with a modular heater device attached to the electrical buss assembly strip in combination with a wicked air freshener.

Similarly, in FIG. 10, is illustrated a modular buss assembly strip 2, having a modular fan assembly, 15, attached thereto, with a modular heater 16, and a wicked air freshener unit, 17. This unit may be plugged into a wall outlet via modular plug element 14, attached to the rear of rotatable plug 6.

Rotatable plug 6 may be fitted to engage an appropriate outlet plug for the country or region in which the device is to be sold and utilized by means of plug module 14. Accordingly, in the United States, where a standard plug having two parallel blades is utilized, the rotatable plug may be attached to a plug module designed to provide two parallel blades. In other countries, a plug module having specific blade configurations may be utilized. Plug module 14 is fitted with contacts to engage contact points 10. Contact may be made using pressure alone, or plug 14 may be equipped with spring loaded contact points so as to ensure continuous electrical contact in use. Typically the rotatable plug assembly 6 accepts a plug module placed on the back of buss 2, and optional device modules are placed on the front side of buss 2. The rotatable plug is significant since outlet orientation may vary from nation to nation, state to state, or region to region. It may be important to maintain the finished unit in a specific orientation for proper operation. For example, it may be necessary to maintain the volatile dispenser unit in a vertical orientation to prevent spillage of liquid compositions contained therein.

When employed, the heater may be of any number of types known in the art. Heaters are generally of a resistance nature and may or may not have control circuitry to regulate temperature. When dispensing a volatile compound, the compound may be present in the form of a gel contained within a membrane as disclosed in U.S. Pat. No. 5,788,185 or a wicking device in proximity to the heater may be utilized such as that disclosed in U.S. Pat. Nos. 5,945,094, 5,903,710 or 5,976,503 which can employ a liquid material. Alternatively mats which contain insecticide or insect repellent may be placed adjacent to the heater so that the active material is volatilized as necessary to obtain an effective insect repelling amount of active in the atmosphere. The heater is desirably modular and is designed with contact points 30 which electrically engage contact points 4 to compete a circuit. Heater may be designed with contact points 30, which are spring loaded to ensure completion of the electrical circuit. The device contemplated herein is designed with a shroud or cover to conceal the components attached to buss 2 so as to prevent tampering, and prevent exposure to live electrical contacts. Auxiliary devices such as fans, lights, on off switches, thermostatic controls, end of use indicator devices, are designed in the same manner as the heater described above. All will have fastening devices to engage hole 3, and all will have contact points which engage plug 4 to complete an electrical circuit. Such devices are known to those skilled in the art and need not be further described herein.

In the manufacture of volatile dispensing devices in accordance with this invention, the base buss assembly strip 2 is equipped with a power source comprising either a rotatable plug 6 or a battery device, not shown. Component devices, including an electrical plug for the country in which the device is intended for sale, can then be simply added to the buss assembly strip by snapping the component device and plug into place. By the use of the buss assembly, having extra electrical contacts by which further modular units may be attached, the rotatable plug 6 allows for the convenient use of the modular assembly, in combination with various heater devices, light devices, and the like from country to country and by consumers having differing needs and/or desires. While skins or shrouds of the device can be modified, to fit local esthetics, other components can be utilized in multiple devices and assembly is simplified by a quick change of modular components in the assembly. By having to stock fewer varieties of finished combined units, and promoting ease of assembly, the ultimate cost to the consumer is lowered. Such component assemblies may be packaged and sold as pre-packaged combinations or as individual components to be combined by the consumer.

With reference to the Figures, it will be apparent that the electrical buss assembly strips of the invention combined with the other components described above provide for electrically powered modular assembly of air care and insect control dispensing units. By the use of the invention, manufacturing costs may be reduced, and product uniformity achieved. While not specifically stated, the buss assembly strips of the invention can also be utilized to provide for the manufacture of other modular type products such as night lights, additional outlets, infra red security systems, and the like. When placement of the extra added plugs need provide for usage of the device in different locations, the modular plugs themselves may be designed to join sequentially with the modular plug designed for use in the country of sale of the device. The above specification is intended to be a brief explanation of the invention, and this specification shall not be interpreted to limit the scope or application thereof.

INDUSTRIAL APPLICABILITY

The present invention provides a means to configure dispensers of volatile compositions, such as air fresheners, insect control compounds, and the like, in a large variety of combinations. By providing a single buss assembly strip having standardized electrical connections, the consumer is enabled to construct a large variety of finished dispensers by choice of individual selected modules providing differing functions. For example, the consumer may combine the buss assembly strip with a modular plug assembly for use in the United States, with optional heaters, night lights, timers, switches, and controls.

What is claimed is:

1. A buss assembly strip for a modular dispenser of volatile materials, comprising an electrically insulating material encompassing parallel offset electrical buss bars, and a rotatable plug assembly comprising electrical contact elements by which electrical power may be transmitted from an external modular plug element which may be directly connected to an electrical circuit, said buss bars offset from each other so as to contact conductive contact rings on the opposite sides of said rotatable plug, said rings being electrically connected to said external modular plug element so as to receive electrical power from said rotatable plug assembly, whereby said buss bars are electrically connected to said rotatable plug and said electrical circuit, and wherein said buss bars have a plurality of sets of electrical contact points along the length of said buss bars whereby modular electrical elements may be connected to said buss assembly strip at any one of a plurality of mounting points.

2. A buss assembly strip according to claim 1, further including mounting means for the attachment of at least one modular electrical element selected from the group consisting of heaters, fans, switches, night lights and controls, at any one of said plurality of mounting points.

3. A modular dispenser for volatile materials, comprising:

a. a buss assembly strip for a modular dispenser of volatile materials, comprising an electrically insulating material encompassing parallel offset electrical buss bars, and a rotatable plug assembly comprising electrical contact elements by which electrical power may be transmitted from an external modular plug element which may be directly connected to an electrical circuit, said buss bars offset from each other so as to contact conductive contact rings on the opposite sides of said rotatable plug, said rings being electrically connected to said external modular plug element so as to receive electrical power from said rotatable plug assembly, whereby said buss bars are electrically connected to said rotatable plug and said electrical circuit, and wherein said buss bars have a plurality of sets of electrical contact points along the length of said buss bars whereby modular electrical elements may be connected to said buss assembly strip at any one of a plurality of mounting points;

b. volatile composition dispersing means; and c. one or more modular components selected from the group consisting of electrical heaters, fans, switches, night lights, and programmable controls, said components being individually capable of being attached to said buss assembly strip at any one of the plurality of mounting points and further comprising electrical contact elements to engage a set of said electrical contact points of said buss assembly strip corresponding to a mounting point.

4. The modular dispenser of claim 3, wherein said rotatable plug is capable of providing continuity of electrical contact and polarity throughout 360 degrees of rotation.

5. The modular dispenser of claim 4, wherein said volatile material is selected from the group consisting of air fresheners and insect control compositions.

6. The modular dispenser of claim 4, wherein said modular plug element is selected so as to engage electrical outlets of a specified region of the world.

7. The modular dispenser of claim 4, wherein said modular components comprise a volatile composition dispensing means and a heater element.

8. The modular dispenser of claim 7, further comprising a modular fan component.

9. The modular dispenser of claim 7, further comprising a modular night light component.

10. The modular dispenser of claim 7, wherein said volatile dispensing means comprises a wick.

* * * * *